United States Patent [19]

Bills et al.

[11] Patent Number: 5,250,424

[45] Date of Patent: Oct. 5, 1993

[54] PROCESSES FOR PREPARING NOVEL SQUALENE SYNTHETASE INHIBITORS

[75] Inventors: Gerald F. Bills, Cranford, N.J.; Maria T. Diez, Madrid, Spain; Mary N. Omstead, Gladstone, N.J.; Fernando Pelaez, Madrid, Spain

[73] Assignee: Merck & Co., Inc., Rahway, N.J.

[21] Appl. No.: 990,158

[22] Filed: Dec. 14, 1992

Related U.S. Application Data

[62] Division of Ser. No. 715,535, Jun. 14, 1991, Pat. No. 5,200,342.

[51] Int. Cl.[5] ........................ C12P 17/18; C12N 1/14; C12R 1/645

[52] U.S. Cl. ................................ 435/119; 435/254.1; 435/911

[58] Field of Search ........................ 435/119, 254, 911

[56] References Cited

U.S. PATENT DOCUMENTS 5,026,554 6/1991 Bartizal et al. ...................... 424/404
5,053,425 10/1991 Bartizal et al. ...................... 514/452
5,055,487 10/1991 Bartizal et al. ...................... 514/452

FOREIGN PATENT DOCUMENTS 450812 3/1991 European Pat. Off. .

OTHER PUBLICATIONS

Database WPIL Week 6800, Derwent Pub. Ltd., London, GB, AN 66-23017F and NL-6 603 344 (Syntex Corp.). (1966).

ATCC Catalogue of Fungi/Yeasts, 17th Edition, p. 128, (1987).

*Primary Examiner*—Herbert J. Lilling
*Attorney, Agent, or Firm*—Christine E. Carty; Melvin Winokur; Joseph F. DiPrima

[57] ABSTRACT

This invention relates to strains of the species *Curvularia lunata* isolated from tree bark and useful in a fermentation process to form compounds of formula (I):

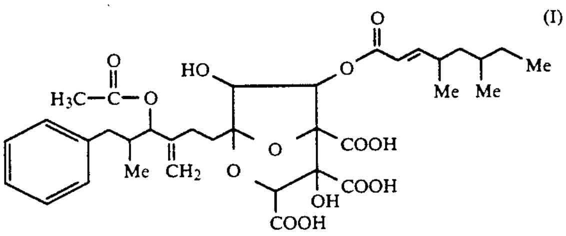

(I)

10 Claims, No Drawings

PROCESSES FOR PREPARING NOVEL SQUALENE SYNTHETASE INHIBITORS

This is a division of application Ser. No. 07/715,535, filed Jun. 14, 1991, now U.S. Pat. No. 5,200,342 issued Apr. 6, 1993.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl T-RNA.

Previous efforts at inhibiting squalene synthetase have employed pyrophosphate or pyrophosphate analog containing compounds such as those described in P. Ortiz de Montellano et al, J. Med. Chem. 20, 243 (1977) and E. J. Corey and R. Volante, J. Am. Chem. Soc., 98, 1291 (1976). S. Biller (U.S. Pat. No. 4,871,721) describeds isoprenoid (phosphinylmethyl)phosphonates as inhibitors of squalene synthetase.

SUMMARY OF THE INVENTION

The present invention provides strains of *Curvularia lunata* that produce nonphosphorous containing inhibitors of squalene synthetase.

DETAILED DESCRIPTION OF INVENTION

The present invention is directed to novel microorganisms that produce compounds of structural formula (I) that are squalene synthetase inhibitors;

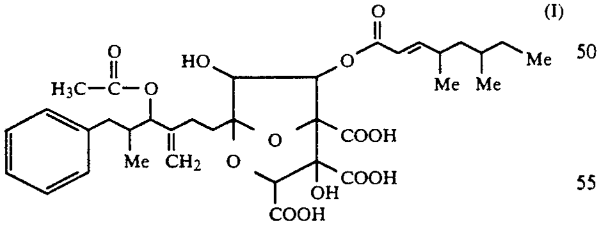

(I)

Compounds of formula (I) and their use as cholesterol-lowering agents and antifungal agents are described in co-pending U.S. patent application Ser. No. 07/496,733 filed Mar. 21, 1990.

The compounds of formula (I) are prepared in an aerobic fermentation of strains of *Curvularia lunata.* More particularly the strains employed may be selected from strains MF5573, MF5572, or a mutant organism thereof.

The culture MF5573, *Curvularia lunata* var. *lunata,* was isolated from *Ficus elastica* tree bark (Philippines).

The culture has been deposited with the American Type Culture Collection (ATCC) at 12301 Parklawn Drive, Rockville, Md. 20852 as ATCC 74067. Culture MF5572 is a strain of *Curvularia lunata* var. *aeria,* isolated from tree bark (Philippines). This culture has been deposited with ATCC as ATCC 74066.

In general, the *Curvularia lunata* strains of the present invention are plurivorous and may be isolated from stems, leaves, bark and seeds of woody and herbaceous plants. These fungi may be readily obtained into axenic cultures by a variety of methods. Most grow moderately fast to rapidly on standard mycological media composed of, but not limited to extracts of cereals, yeast extracts, fruit extracts, leaf extracts, simple sugars, polysaccharides, amino acid, or protein hydrolyzates. The simplest and most direct method of isolating strains of *C. lunata* is to collect infested plants that have fungal conidiophores and conidia already developed on the plant surface or which are associated with plant lesions. Conidia can be aseptically transferred to common mycological media to initiate a culture. Another method is to collect recently dead, moribund or senescent plant organs and incubate them in a moist chamber until conidia and conidiophores develop, and then transfer the conidia to a nutrient medium with a sterile dissecting tool. A third method takes advantage of the abundance of *C. lunata* in the environment; due to their often prolific conidium production, strains of *Curvularia lunata* may also be recovered from common organic substrata such as soil, dung, or leaf litter. Small amounts of these substrata can be serially diluted and the dilution applied to mycological media containing antibacterial antibiotics. Colonies of *Curvularia lunata* develop rapidly and can be easily distinguished from colonies of fungi developing from the dilution by their distinctive conidia. Another, more specific method of isolation is based on the fact that the mycelia of *C. lunata* colonize tissues that underly the outer surfaces of plants. By sterilizing the surface of the plant sample prior to its incubation on selective agar medium, many undesirable fungi and bacteria are eliminated and colonies of *C. lunata* are more readily detected.

Strains of *Curvularia lunata* exhibit the following morphological characteristics.

Colonies relatively fast-growing , in 1 week attaining a diameter of: 35–40 mm on cornmeal agar (Difco Laboratories); 40 mm on yeast-malt extract agar (10 g malt extract, 2 g yeast extact, 20 g agar in 1 L distilled water), 45–50 mm on V8 juice agar (200 mL V8 juice, Campbell Soup Co., 3 g $CaCO_3$, 20 g agar diluted to 1 L distilled water). On yeast-malt agar with both submerged and aerial mycelium, sometimes forming radial strands, floccose to cottony or lanose in age, with margin appressed, minutely fimbriate, hyaline to pale gray at the margin but soon darkening to dark gray or dark olive-gray, Castor Gray, Dark Olive-Gray, Iron Gray, Dusky Green-Gray, Blackish Green-Gray, Olivaceous Black (capitalized color names from Ridgway, R. 1912. *Color Standards and Nomenclature,* Washington, D.C.), similar in reverse, often with patches or tufts of hyaline to pale gray aerial hyphae developing in older portions, occasionally forming pale gray to hyaline sectors. Odors, sclerotia, stromata, or pseudothecia absent.

Conidiophores arising from surface or aerial hyphae, 15–250×3–5 Km, septate, straight or flexuous, sometimes branched in age, with apices straight, curved or geniculate, smooth, thin- to slightly thick-walled, olive-brown to olive-gray in 3% KOH, bearing 4–15 conidia. Conidiogenous cells polytretic, integrated, indeterminate, sympodial, usually terminal on the conidiophore, sometimes intercalary in-age, with slightly darkened scars surrounding a minute pore at the conidiogenous locus. Conidia 21–30×9–13.5 μm, usually 3-septate, infrequently 4-septate, broadly elliptical, with penultimate, distal cell curved and often obliquely swollen, with slightly flattened scar at base, without hilar appendix, smooth pale olive-brown to olive-gray, usually with two central cells slightly darker. Hyphae pale olive-gray to dark olive-gray or olive-brown in 3% KOH, septate, branched.

The genus Curvularia is distinguished from other fungal genera by the combination of polytretic conidiogenesis cells that give rise to predominately 3–4-septate, dematiaceous phragmoconidia, and conidia with a non-protruding, rounded hilum, and a curved, swollen penultimate cell. Within the genus Curvularia, the *lunata* species is distinguished by conidia that are relatively short (<30 μM) and usually 3-septate, curved and smooth. *Curvularia lunata* var. *lunata* is the type species of the genus Curvularia and is characterized by the absence of formation of stromata in culture. The variety *aeria* of *Curvularia lunata* is distinguished from the type variety by the formation of stromata in culture.

A biologically pure culture of *Curvularia lunata* as claimed herein is defined as being isolated from the natural environment and free of viable contaminating microorganisms. A culture of *Curvularia lunata* as claimed herein is defined as being isolated from the natural environment and free of viable contaminating microorganisms that would be deleterious to the formation of a compound of formula (I).

Although in general the formation of a particular secondary metabolite is unpredictable, Applicants have surprisingly found that strains of *Curvularia lunata* are chemotaxonomically similar in their ability to produce inhibitors of squalene synthetase which are compounds of formula (I). These strains are readily detected by a rapid two-stage screening procedure. Strains are isolated and cultivated in liquid nutrient media. Small samples are removed periodically and the final fermentation broth is frozen and stored. The small samples are used in the first stage of the screening procedures. The samples are extracted with an organic solvent. The organic phase is concentrated and tested in the squalene synthetase assay described below. The presence of a compound that inhibits the activity of squalene synthetasellis determined by comparing the squalene synthetase activity of the sample to the squalene synthetase activity of the control. Fermentation broths which give a positive result in the squalene synthetase assay are tested in the second stage of the screening procedure. The frozen fermentation broth is thawed and extracted with an organic solvent. The organic phase is concentrated and analyzed by high performance liquid chromatography (HPLC). The presence of compounds of formula (I) is determined by comparing the chromatogram of the extracted sample to the chromatogram of authentic (I).

*Curvularia lunata* var. *lunata* MF5573 was recovered from the bark of *Ficus elastica* collected in Diliman, Qubzon City, Philippines. Bark discs were removed with a leather punch (no. 245, C.S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate., 50 mg chlorotetracycline, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5573 has been identified as *Curvularia lunata* var. *lunata* and exhibits the following morphological characteristics.

Colonies are relatively fast-growing, in 1 week attaining a diameter of: 35–40 mm on cornmeal agar (Difco Laboratories); 40 mm on yeast-malt extract agar (10 g malt extract, 2 g yeast extract, 20 g agar in 1 L distilled water); 45–50 mm on V8 juice agar (200 mL V8 juice, Campbell Soup Co., 3 g $CaCO_3$, 20 g agar diluted to 1 L distilled water). 0n yeast-malt agar both submerged and aerial mycelia form, with aerial mycelia sometimes forming radial strands, floccose to cottony or lanose in age, with margin appressed, minutely fimbriate, hyaline to pale gray at the margin but soon darkening to dark gray or dark olive-gray, Castor Gray, Dark Olive-Gray, Iron Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions, occasionally forming pale gray to hyaline sectors, odors, sclerotia, stromata, or pseudothecia absent.

Conidiophores arising from surface or aerial hyphae, 15–250×3–5 μm, septate, straight or flexuous, sometimes branched in age, with apices straight, curved or geniculate, smooth, thin- to slightly thick-walled, olive-brown to olive-gray in 3% KOH, bearing 4–15 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 21–30×9–13.5 pm, usually 3-septate, infrequently 4-septate, broadly elliptical, with penultimate, distal cell curved and often obliquely swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched.

Strain MF5572, was recovered from the bark of an unidentified tree, collected in Diliman, Quezon City, Philippines. Bark discs were removed with a leather punch (no. 245, C.S. Osborne & Coi, Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were shaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 240° C., and inspected more or less daily for up to two weeks for the development of fungal colonies on bark discs and the agar.

Strain MF5572 has been identified as *Curvularia lunata* var. *aeria* and exhibit the following morphological characteristics.

Colonies are relatively fast-growing, in 1 week attaining a diameter of: 30–35 mm on cornmeal agar (Difco Laboratories); 30–35 mm on yeast-malt extract agar (10 g malt extract, 2 g yeast extract, 20 g agar in 1 L distilled water); 40–55 mm on V8 juice agar (200 mL V8 juice, Campbell Soup Co., 3 g $CaCO_3$, 20 g agar diluted to 1 L distilled water). On yeast-malt agar both submerged and aerial mycelia form, are slightly raised in side view, velvety to floccose when young, cottony or lanose in age, with margin slightly raised, even to wavy, hyaline to pale gray at the margin but soon darkening to grayish olive, gray, to dark olive-gray, Smoke Gray, Light Grayish Olive, Deep Olive-Gray, Dark Olive-Gray, Iron Gray, Castor Gray (capitalized color names from Ridgway, R. 1912. Color Standards and Nomenclature, Washington, D.C.), in reverse yellowish gray towards the margin but soon olivaceous gray, in age developing dark olive-black spots and patches in the agar, often with patches or tufts of hyaline to pale gray aerial hyphae developing in older portions, odors and pseudothecia absent. The surface of cultures in excess of 3 weeks old, generally develop straight to curved, cylindrical, finger-like stromata, 0.5–1 mm tall, which project upward from the oldest regions of the colony surface. Stromata formation is best on nutrient-rich media, e.g. potato-dextrose agar, oatmeal agar, or glucose-yeast-malt extract agar.

Conidiophores arising from aerial hyphae, 30–200×3–5 μm, septate, straight or flexuous, sometimes branched in age, with apices straight, curved or geniculate, smooth, thin- to slightly thick-walled, olive-brown to olive-gray in 3% KOH, bearing 2–10 conidia. Conidiogenous cells polytretic, integrated, indeterminate, sympodial, usually terminal on the conidiophore, sometimes intercalary in-age, with slightly darkened scars surrounding a minute pore at the conidiogenous locus. Conidia 18–28×9–14 btm, consistently 3-septate, broadly elliptical, with penultimate, distal cell curved and distinctly swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched. Stromatic tissue a textura intricate, with cells hyaline in 3% KOH.

Compounds of formula (I) can be obtained by cultivation of fungal microorganisms in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (e.g., ammonium nitrate, ammonium sulfate, ammonium phosphate, etc.) can also be used. The various sources of nitrogen can be used alone or in combination in amounts ranging between 0.2 to 90 percent by weight of the medium. , The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like. Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperature ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 50 days, preferably 14 to 30 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.5 to 8.5, most preferably 4.5 to 7.0. After the appropriate period for production of the desired compound, fermentation flasks are harvested and the active compound isolated.

The pH of the aqueous mycelial fermentation is adjusted to between 1 and 9 (preferably between 3 and 5) preferably mixed with a water miscible solvent such as methanol and the mycelia filtered. The active compound may then be isolated from the aqueous filtrate by several methods including:

1. Liquid-liquid extraction of the aqueous filtrate into a water immiscible solvent such as methyl elthyl ketone, ethyl acetate, diethyl ether, or dichloromethane preferably after having adjusted the pH to between 3 and 5.

2. Solid-liquid extraction of the aqueous filtrate onto an organic matrix such as SP207 or HP-20 and elution with an organic solvent (aqueous or non aqueous) such as 90/10 methanol/water or 90/10 acetone/water.

3. Adsorption of the active compound from the aqueous filtrate onto an ionic exchange resin such as Dowex 1($Cl^-$) and elution with a high ionic strength organic-/aqueous solvent such as 90/10 methanol/aqueous 30% $NH_4Cl$. This material could then be desalted by employing either method 1 or 2 above. Each of these three methods may also be used in the further purification of the active compound.

The fraction containing active compound from the above methods could then be dried in vacuo leaving the crude active compound. The crude active compound is then generally subjected to several separation steps such as adsorption and partition chromatography, and precipitation. For each separation step, fractions are collected and combined based on results from an assay and/or HPLC analysis.

The chromatographic separations may be carried out by employing conventional column chromatography with ionic or nonionic adsorbent. When silica gel is the adsorbent, an alcohol/chlorohydrocarbon/organic acid mixture such as methanol/chloroform/acetic acid/water is useful as an eluant. For reverse phase chromatography, the preferred adsorbent is a $C_8$ or $C_{18}$ bonded phase silica gel. The preferred eluant for reverse phase chromatography is a mixture of acetonitrile and water buffered at a low pH, such as 0.1% phosphoric acid, or trifluoroacetic acid. The active compound can be precipitated out of a non-polar solvent as the quinine salt. The preferred solvent for precipitation is diethyl ether.

The intrinsic squalene synthetase inhibitory activity of the compounds formed in the fermentation of the microorganisms of the present invention may be measured by the standard in vitro protocol described below:

PREPARATION OF RAT LIVER MICROSOMES

Male, Charles River CD rats (120 to 150 g) were fed a diet containing 0.1% lovastatin for 4 days. The livers from these rats were homogenized in 5 volumes (mL/g) of ice cold 50 mm HEPES (4-(2-hydroxyethyl)-1-piperazine-ethanesulfonic acid), 5 mm EDTA(ethylenediaminetetraacetic acid) pH 7.5 with a Potter-Elvehjem type tissue grinder. The homogenate was centrifuged twice at 20,000×g for 15 min. at 4° C., discarding the pellet each time. The supernatant was then centrifuged at 100,000×g for 1 hr. at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

PARTIAL PURIFICATION OF PRENYL TRANSFERASE

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 mm leupeptin, 0.005% phenylmethyl sulfonyl fluoride pH 7.0 containing 0.1 trypsin inhibitor units of aprotinin/mL. The homogenate was centrifuged at 20,000×g for 20 min. The supernatant was adjusted to pH 5.5. with 6 N HOAC and centrifuged at 100,000×g for 1 hour. This supernatant was adjusted to pH 7.0 with 3 N KOH and a 35–60% ammonium sulfate fraction taken. The 60% pellet was redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 mL of Buffer A and a 1 liter gradient from Buffer A to 100 mm potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mm Tris, 10 mm β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

ENZYMATIC SYNTHESIS OF [4$^{14}$C]FARNESYL-PYROPHOSPHATE

The solvent (ethanol: 0.15 N $NH_4OH$, 1:1) was removed from 55 mCi of (4–14C]isopentenyl pyrophosphate(47.9 mci/mmole) by rotary evaporation. Six hundred microliters of 100 mm Tris, 10 mm $MgCl_2$, mM dithiothreitol pH 7.5 was added and the solution was transferred to a 1.5 mL Eppendorf centrifuge tube. Geranyl-pyrophosphate, 250 ml of a 20 mm solution, and 50 ml of the ammonium sulfate suspension of prenyl transferase were added to initiate the reaction. This incubation contained 5 mmoles of geranyl pyrophosphate, 1.15 mmoles of isopentenyl pyrophosphate, 6 mmoles of MgCl2 of 0.18 units of prenyl transferase in a volume of 900 ml. The incubation was conducted at 37° C. During the incubation, the mix turned cloudy white as the newly formed magnesium complex of farnesyl pyrophoshate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mm HEPES, 5 mm EDTA, pH 7.5 The yield was 50.7 mCi (92%) of [4-

[14]C]farnesyl pyrophosphate. The [4-$^{14}$C]farnesyl pyrophosphate was stored in aliquots at −70° C.

SQUALENE SYNTHETASE ASSAY

Reactions were performed in 16×125 mm screw cap test tubes. A batch assay mix was prepared from the following solution:

| | mL per assay | volume for 50 assays |
|---|---|---|
| 1. 250 mM HEPES pH 7.5 | 20 | 1000 |
| 2. NaF 110 mM | 10 | 500 |
| $MgCl_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 mCi/mmole, and 0.025 mCi/3.0 mL | 3.0 | 150 |
| 7. $H_2O$ | 24 | 1200 |

This assay mix was degassed under a vacuum and flushed with $N_2$. Solutions of the squalene synthetase inhibitors were prepared either in DMSO or MeOH and a 1:120 dilution of the microsomal protein was made with the original homogenizing buffer. For each reaction, 87 mL of the assay mix was taken with 3 ml of an inhibitor solution (DMSO or MeOH in the controls), warmed to 30° C. in a water bath and then the reaction was initiated by the addition of 10 mL of the 1:120 dilution of microsomal protein (0.6 mg protein total in the assay). The reactions were stopped after 20 minutes by the addition of 100 mL of a 1:1 mix of 40% KOH with 95% EtOH. The stopped mix was heated at 65° C. for 30 min., cooled, 10 mL of heptane was added and the mix was vortexed. Two g of activated alumina was then added, the mix vortexed again, the alumina allowed to settle and 5 mL of the heptane layer was removed. Ten mL of scintillation fluid was added to the heptane solution and radio-activity was determined by liquid scintillation counting.

Percent inhibition is calculated by the formula:

$$1 - \frac{[\text{Sample} - \text{Blank}]}{[\text{Control} - \text{Blank}]} \times 100$$

The composition of media employed in the following Examples are listed below.

| Component | Amount |
|---|---|
| Yeast Extract | 4.0 g |
| Malt Extract | 10.0 g |
| Glucose | 4.0 g |
| Distilled $H_2O$ | 1000 mL |
| Agar | 25.0 g |

KF SEED MEDIUM

| | per liter | Trace Element Mix | g/L |
|---|---|---|---|
| Corn Steep Liquor | 5 g | $FeSO_4.7H_2O$ | 1.0 |
| Tomato Paste | 40 g | $MnSO_4.4H_2O$ | 1.0 |
| Oat Flour | 10 g | $CuCl_2.2H_2O$ | 0.025 |
| Glucose | 10 g | $CaCl_2.2H_2O$ | 0.1 |
| Trace Element Mix | 10 ml | $H_3BO_3$ | 0.056 |
| pH adjusted to 6.8 (presterile) | | $(NH_4)_6Mo_7O_{24}.4H_2O$ | 0.019 |
| 50 mL/nonbaffled 250 mL | | $ZnSO_4.7H_2O$ | 0.2 |
| Erlenmeyer flask | | dissolved in 1 L 0.6N HCl | |
| autoclave 20 min. (121° C., 15 psi) | | | |

Production Media

BRF

| | |
|---|---|
| Brown rice | 5.0 g/nonbaffled 250 mL Erlenmeyer flask |
| Base liquid #2 | 20.0 mL/flask |

Base liquid #2

| | g/L |
|---|---|
| Yeast extract | 1.0 |
| Sodium tartrate | 0.5 |
| $KH_2PO_4$ | 0.5 |
| distilled water | 1000.0 mL |
| (no pH adjustment) | |
| autoclave 15 min. (121° C., 15 psi) | |
| add 15.0 mL distilled $H_2O$/flask | |
| autoclave 20 min. (121° C., 15 psi) | |

F1 medium

| | |
|---|---|
| Cracked corn | 10.0 g/nonbaffled 250 mL Erlenmeyer flask |
| Base liquid #3 | 10.0 mL/flask |

Base liquid #3

| | g/L |
|---|---|
| Ardamine PH | 0.2 |
| $KH_2PO_4$ | 0.1 |
| $MgSO_4.7H_2O$ | 0.1 |
| Sodium tartrate | 0.1 |
| $FeSO_4.H_2O$ | 0.01 |
| $ZnSO_4.7H_2O$ | 0.01 |
| distilled $H_2O$ | 1000.0 mL |
| (no pH adjustment) | |
| autoclave 15 minutes (121° C., 15 psi) | |
| add 15.0 mL distilled $H_2O$ | |
| autoclave 20 minutes (121° C., 15 psi) | |

LSF1 medium

| | g/L |
|---|---|
| Glycerol | 75.0 |
| Glucose | 10.0 |
| Ardamine PH | 5.0 |
| Soybean meal | 5.0 |
| Tomato paste | 5.0 |
| Sodium citrate | 2.0 |
| $(NH_4)_2SO_4$ | 2.0 |
| Presterile pH adjusted to 7.0 | |
| add 45 mL/nonbaffled 250 mL Erlenmeyer flask | |
| autoclave 20 min (121° C., 15 psi) | |

The following examples illustrate the preparation of compounds of formula (I) and are not to be considered as limiting the invention set forth in the claims hereto.

EXAMPLE 1

A. Culturing MF5573

Culture MF5573 was inoculated into KF seed medium using one glass scoop of a mixture of spores and hyphae that had been preserved in sterile soil. The KF seed flask was incubated for 66 hr at 25° C., 220 rpm, 85% humidity. At the end of this incubation, 2.0 mL aliquots were aseptically transferred to each of 25 Fl solid production medium flasks. These production flasks were then incubated at 25° C. statically for 26 days. At harvest 45 mL of 70% methanol were added to each flask and the solid growth was manually broken apart into smaller pieces. Flasks were than placed onto a gyrotory shaker and agitated at 220 rpm for 30 minutes in order to further break up the mycelial mass as well as to improve contact of the solvent with the cells. After shaking, the contents of the individual flasks were pooled by pouring the entire contents of the flasks (solids and all) into a 2 L beaker.

B. Isolation of Compound I

One liter of methanol was added to the 70% methanol extract of the solid fermentation from 25 flasks and the resulting mixture was stirred vigorously. After stirring, the mixture was filtered to yield 1900 mL of filtrate and the spent mycelium was reextracted with an additional two liters of methanol, stirred and filtered to yield a second 1850 mL of filtrate.

A 750 mL portion of each of these filtrates was combined and the mixture was diluted with 1500 mL water. This three liter feed was absorbed onto a 300 mL Dowex 1 ($CL^-$) column at 30 mi/min., washed with 500 ML $CH_3CN/H_2O$ (60:40), and eluted with one liter $CH_3CN$/0.05M citrate buffer pH=5.5, followed by one liter $CH_3CN$/0.05M citrate buffer pH=4.0 and one liter $CH_3CN$/0.05M citrate buffer pH=3.0.

The one liter CH3CN/0.05M citrate buffer pH=3.0 eluate was concentrated to ~600 mL, diluted to 1500 mL with water, and adjusted to pH=4. This preparation was adsorbed to 100 mL HP-20 at 10 mi/min., washed with water and with methanol/$H_2O$ (50:50), and eluted with 100% methanol.

The 100% methanol eluate was concentrated to dryness, reconstituted in 1 mL $CH_3CN$/aqueous $H_3PO_4$ pH=2.5 (60:40) and 100 μl of this preparation was chromatographed on a 0.9×25 cm Phenomenex (30% carbon loaded) C18 column using a $CH_3CN$/aqueous $H_3PO_4$ pH=2.5 (60:40) mobile phase. Fractions that were active in the squalene synthetase assay were shown to contain Compound (I).

EXAMPLE 2

A. Culturing MF5572

Culture MF5572 was inoculated into KF seed medium using one glass scoop to a mixture of spores and hyphae that had been preserved in sterile soil. The KF seed flask was incubated for 49 hrs at 25° C. 220 rpm, 85% humidity. At the end of this incubation, 2.0 mL aliquots were aseptically transferred to each of 19 BRF solid production medium flasks and 15 LSF1 liquid production medium flasks. These production flasks were then incubated at 25° C., 85% humidity, either statically (BRF flasks) or on a gyrotory shaker at 220 rpm (LSF1 flasks) for 41 days. At harvest 50 mL of methyl ethyl ketone were added to each BRF production flask and the solid growth was manually broken apart into smaller pieces. Each LSF1 flask was extracted with 45 mL of 100% methanol. After solvent addition, flasks were placed onto a gyrotory shaker and agitated at 220 rpm for 30 minutes in order to further break apart the mycelial mass of the BRF flasks, as well as to improve contact of the solvent with the cells. After shaking, the contents of flasks of the same medium type were pooled by pouring the entire contents of the flasks (solids and all) into two 1 L flasks.

B. Isolation of Compound I

Thirteen flasks, to which 50 mL of methyl ethyl ketone per flask had been added, were combined, filtered, and stored under refrigeration. In storage, the volume of this composite was reduced to 275 mL due to evaporation. The pH of a 100 mL portion of this extract was adjusted to 3.0 and extracted with 100 mL ethyl acetate.

Five mL of the 100 mL ethyl acetate extract was concentrated to dryness and reconstituted in 0.5 mL $CH_3CN$/aqueous $H_3PO_4$ pH=2.5 (60:40). This preparation was filtered to remove insolubles and 250 μl of the filtrate was chromatographed on a 0.9×25 cm Phenomenex (30% carbon loaded) C18 column using a $CH_3CN$/aqueous $H_3PO_4$ pH=2.5 (60:40) mobile phase. Fractions that were active in the squalene synthetase assay were shown to contain Compound (I).

What is claimed is:

1. A process for making a compound of structure:

(I)

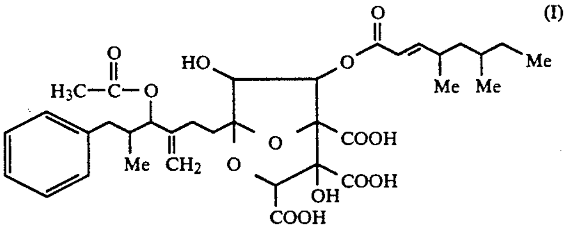

comprising cultivating *Curvularia lunata* under conditions suitable for formation of the compound and recovering the compound.

2. A process of claim 1 wherein the cultivation is carried out for 25–42 days.

3. A process of claim 1 wherein the strain of *Curvularia lunata* is selected from the group consisting of:

a) *Curvularia lunata* var. *lunata*, and b) *Curvularia lunata* var. *aeria*.

4. A process of claim 3 wherein the cultivation is carried out for 25–42 days.

5. A process of claim 1 wherein the strain of *Curvularia lunata* is selected from the group consisting of:

a) MF5573 (ATCC 74067), b) MF5572 (ATCC 74066), or an active mutant thereof.

6. A process of claim 5 wherein the cultivation is carried out for 25–42 days.

7. A process of claim 1 wherein the strain of *Curvularia lunata* is MF5573 (ATCC 74067).

8. A process of claim 7 wherein the cultivation is carried out for 25–42 days.

9. A process of claim 1 wherein the strain of *curvularia lunata* is MF5572 (ATCC 74066).

10. A process of claim 9 wherein the cultivation is carried out for 25–42 days.

* * * * *